(12) United States Patent
Phillips et al.

(10) Patent No.: US 7,476,046 B2
(45) Date of Patent: Jan. 13, 2009

(54) APPLICATOR AND MATERIAL DISPENSING SYSTEM

(75) Inventors: Paul Phillips, Middlebury, CT (US); Ryan Dubey, Hamden, CT (US); Randall Drumm, Renton, WA (US); Dave Martin, Torrington, CT (US)

(73) Assignee: Centrix, Inc., Shelton, CT (US)

( * ) Notice: Subject to any disclaimer, the term of this patent is extended or adjusted under 35 U.S.C. 154(b) by 484 days.

(21) Appl. No.: 11/102,955

(22) Filed: Apr. 11, 2005

(65) Prior Publication Data

US 2006/0228159 A1    Oct. 12, 2006

(51) Int. Cl.
*A46B 11/00* (2006.01)

(52) U.S. Cl. .................. 401/132; 401/123; 401/125

(58) Field of Classification Search ........... 401/118, 401/123, 125, 126, 128, 129, 130, 132, 133; 206/209; 15/176.4, 176.1, 191.1
See application file for complete search history.

(56) References Cited

U.S. PATENT DOCUMENTS

| | | | |
|---|---|---|---|
| 3,386,792 A | 6/1968 | Ireland | 401/40 |
| 4,384,645 A | 5/1983 | Manfredi | 206/229 |
| 4,492,305 A | 1/1985 | Avery | 206/210 |
| 4,732,287 A * | 3/1988 | Bennett | 215/49 |
| 4,880,111 A * | 11/1989 | Bagwell et al. | 206/209.1 |
| 5,001,803 A | 3/1991 | Discko, Jr. | 15/167.1 |
| 5,109,979 A | 5/1992 | Cole | 206/229 |
| 5,150,495 A * | 9/1992 | Discko et al. | 15/167.1 |
| 6,049,934 A | 4/2000 | Discko | |
| 6,059,570 A | 5/2000 | Dragan et al. | |
| 6,099,307 A | 8/2000 | Discko, Jr. | |
| 6,186,792 B1 | 2/2001 | Discko, Jr. | 433/220 |
| 6,283,933 B1 | 9/2001 | D'Alessio et al. | |
| 6,328,159 B1 | 12/2001 | Diskco, Jr. | |
| 6,372,313 B1 | 4/2002 | D'Alessio et al. | 428/34.1 |
| 6,382,972 B1 | 5/2002 | Fishcer et al. | |
| 6,413,087 B1 | 7/2002 | Petrich et al. | 433/89 |
| 6,450,717 B1 | 9/2002 | Salz et al. | 401/125 |
| 6,516,947 B1 | 2/2003 | Van Dyke et al. | 206/361 |
| 6,592,280 B2 | 7/2003 | Petrich et al. | 401/126 |
| 6,634,051 B1 | 10/2003 | Dragan et al. | 15/106 |
| 6,685,013 B2 | 2/2004 | Discko, Jr. | 206/229 |
| 6,957,958 B2 * | 10/2005 | Rowe et al. | 433/89 |

* cited by examiner

*Primary Examiner*—David J Walczak
(74) *Attorney, Agent, or Firm*—Fattibene and Fattibene; Paul A. Fattibene; Arthur T. Fattibene

(57) ABSTRACT

An applicator and material dispensing system having an applicator frictionally retained within an applicator holder and the applicator holder frangibly attached to a material holder. Material placed within the material holder is initially sealed by a frangible portion adjacent one end of the applicator holder. Upon separation of the applicator holder from the material holder the material contained therein is exposed permitting the applicator, upon removal from the applicator holder, to be used to dispense the material. The invention is particularly well suited to dispensing small quantities of dental material.

21 Claims, 4 Drawing Sheets

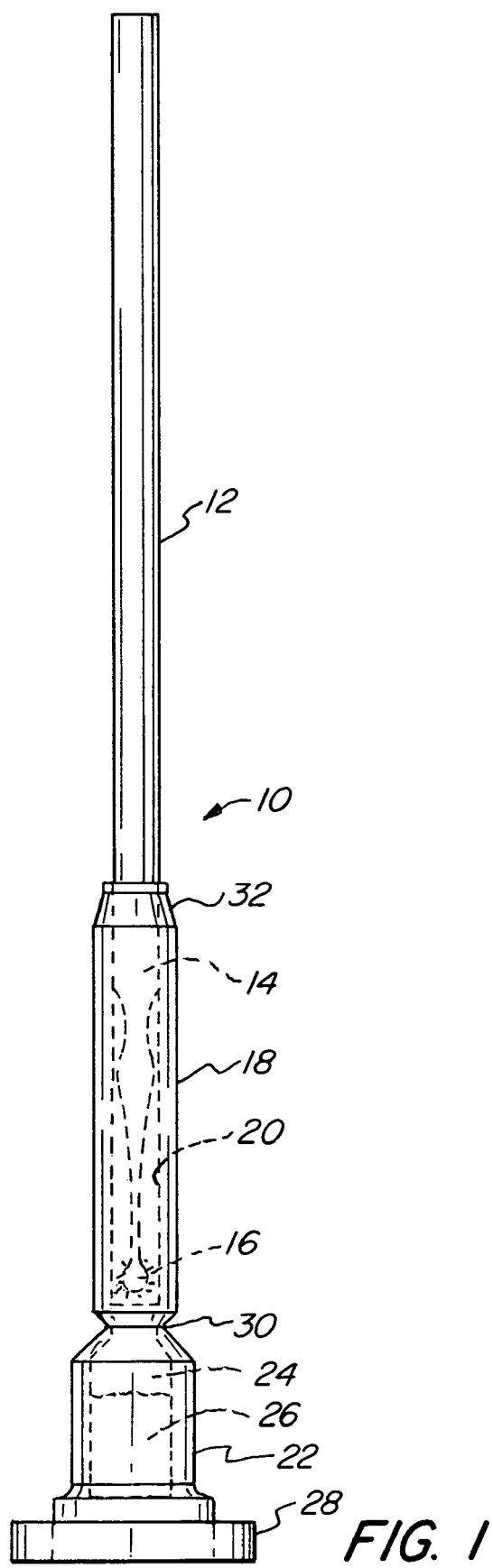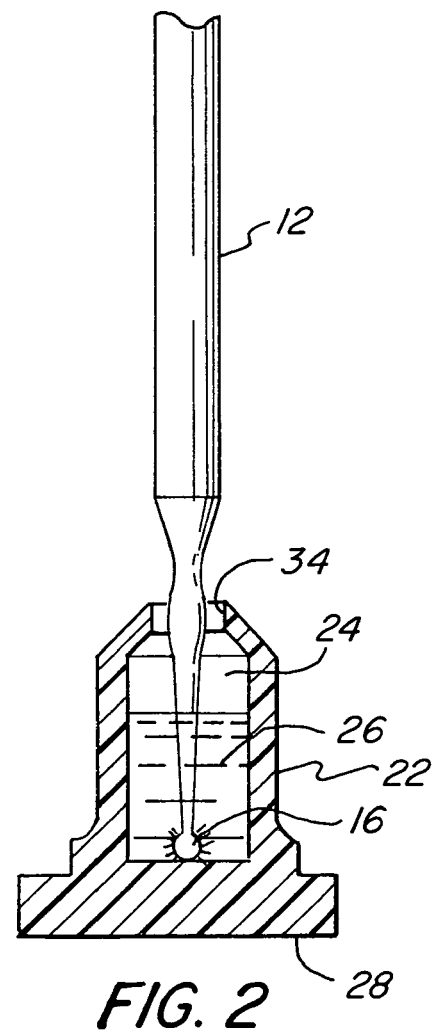
FIG. 1
FIG. 2

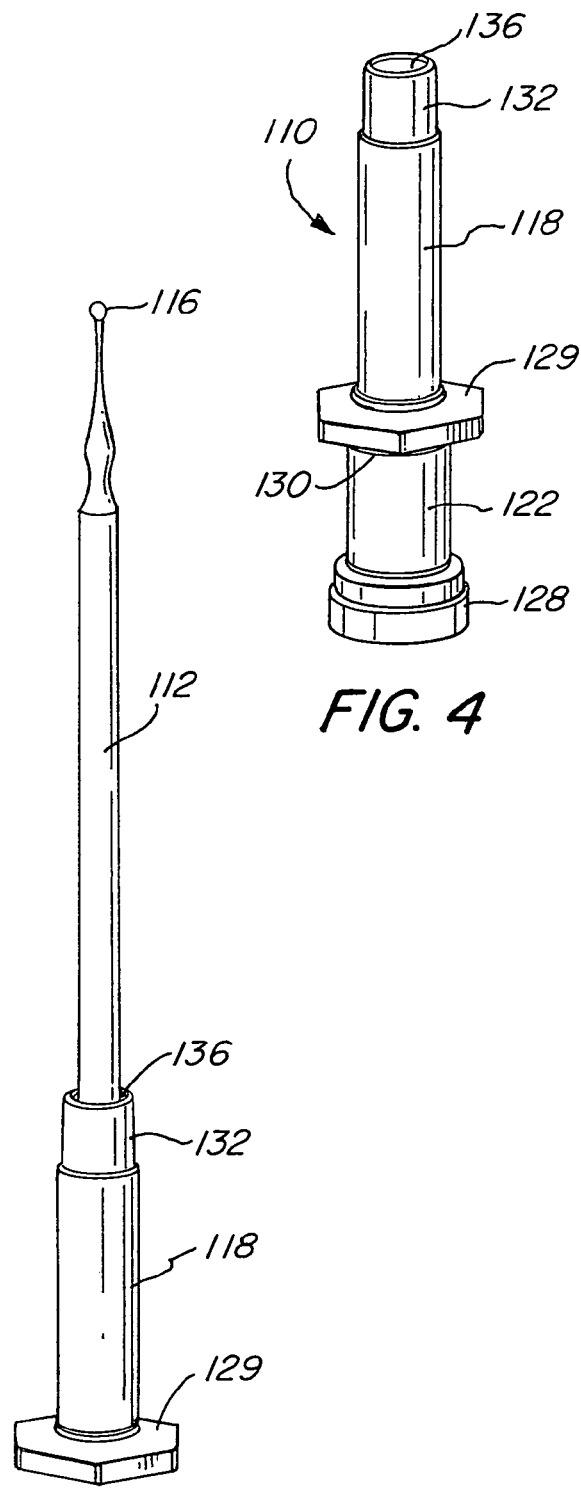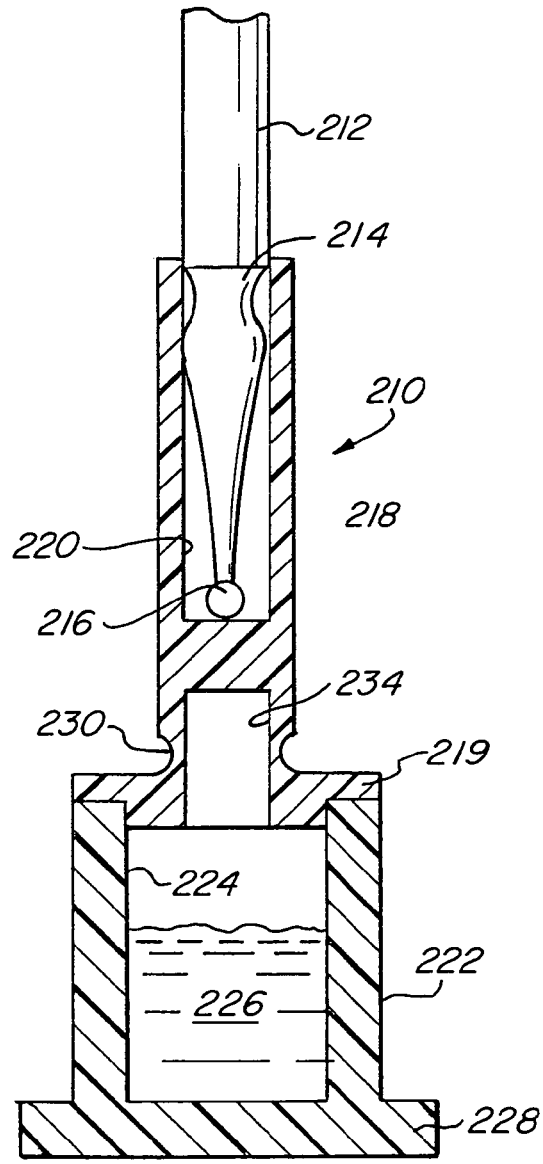
FIG. 4
FIG. 5
FIG. 6

APPLICATOR AND MATERIAL DISPENSING SYSTEM

FIELD OF THE INVENTION

The present invention relates in general to a unit dose applicator and more particularly to an applicator and initially attached material container for applying a small quantity of material.

BACKGROUND OF THE INVENTION

There are many different kinds of applicators used to dispense a material applied to a surface. Many of these materials to be applied are medicaments or, in particular, dental materials used during a medical or dental procedure. One such applicator type device containing a material is disclosed in U.S. Pat. No. 6,059,570 entitled "Dental Container Type Applicator" and issuing to Dragan et al on May 9, 2000. Therein disclosed is a dental container type applicator in the form of a capsule. The material is extruded from the capsule and applied with the aid of minute fibers or flocking adhered to the discharge nozzle.

Another applicator type capsule is disclosed in U.S. Pat. No. 6,099,307 entitled "Dental Capsule for Containing and Dispensing Low Viscosity Dental Material and Method of Filing and Applying said Low Viscosity Material" and issuing to Discko, Jr. on Aug. 8, 2000. Therein disclosed is a dental capsule for dispensing low viscosity or liquid like dental materials. A sponge or cellular foam like material is contained within the body portion of the capsule. A displaceable piston is used to compress the saturated sponge or cellular foam like material to dispense the liquid or low viscosity material.

Another applicator for applying a material is disclosed in U.S. Pat. No. 6,382,972 entitled "Cushioned, Fiber-Covered Dental Delivery Tips" issuing to Fischer et al on May 7, 2002. Therein disclosed are various applicators or tips for dispensing or applying a dental material. In one embodiment, a material is contained within a portion of the applicator. Upon displacing a piston like portion of the applicator, a material is forced through a channel and through the tip of the applicator Another applicator is disclosed in U.S. Pat. No. 6,413,087 entitled "Packaged Applicator Assembly" issuing to Petrich et al on Jul. 2, 2002. Therein disclosed is an applicator having a tip and a cap initially extending over the tip and detachably connected to the applicator. A sponge contained within a cap contains a composition that is transferred to the tip.

While many of these applicators have served their purpose, they are not convenient in some applications where it may be required to initially separate the applicator portion from the material until ready for use.

SUMMARY OF THE INVENTION

The present invention provides a system for storing a small quantity of material in an initially sealed material chamber in combination with an applicator that is protected from contamination. An applicator holder is removably placed on a material holder having a material chamber. A frangible portion is placed between the material holder and the applicator holder so that upon removal of the applicator holder, a material chamber in the material holder may be accessed by the applicator end of the applicator. The material contained within the material chamber may be applied by the applicator once the applicator is removed from the applicator holder. One end of the applicator holder may serve as a seal that fits within the opening formed in the material chamber.

In another embodiment, an applicator and first material holder may hold a quantity of first material, such as a powder, and the applicator. A second material holder is frangibly connected to the first material holder so that upon separation, the first material may be combined with the second material resulting in a predetermined reaction for application of the activated material with the applicator.

In another embodiment, the applicator holder has a cap that initially seals the material chamber. Upon frangibly separating the applicator holder a passage is formed for access to the material chamber.

Accordingly, it is an object of the present invention to provide a material holder and applicator system that can be easily stored and conveniently used to apply a small quantity of material.

It is a further object of the present invention that the applicator end is protected from contamination.

It is yet another object of the present invention that the material to be applied does not contact the applicator until ready for application.

It is an advantage of the present invention that the material to be applied is held in a separate sealed chamber that can be easily unsealed.

It is yet another advantage of the present invention that the material holder and the applicator holder are initially kept together until separated providing access to the material chamber.

It is a feature of the present invention that a frangible portion is placed between the material holder and the applicator holder.

It is another feature of the present invention that one end of the applicator holder may be used to reseal the material chamber in the material holder.

It is another feature of the present invention that one end of the applicator holder is adapted to hold the handle of the applicator in between applications of material.

These and other objects, advantages, and features will become more readily apparent in view of the following detailed description.

BRIEF DESCRIPTION OF THE DRAWINGS

FIG. 1 is an elevational view illustrating the applicator and material dispensing system of the present invention.

FIG. 2 is a partial cross section schematically illustrating the material holder in applying the material to the applicator.

FIG. 4 is a perspective view illustrating another embodiment of the present invention that may be utilized for containing two different materials to be mixed.

FIG. 5 is a perspective view illustrating use of the applicator holder for holding the applicator upright between uses.

FIG. 6 is a cross section of another embodiment of the present invention illustrating a modified construction.

DETAILED DESCRIPTION OF THE PREFERRED EMBODIMENT

Figure 3A:
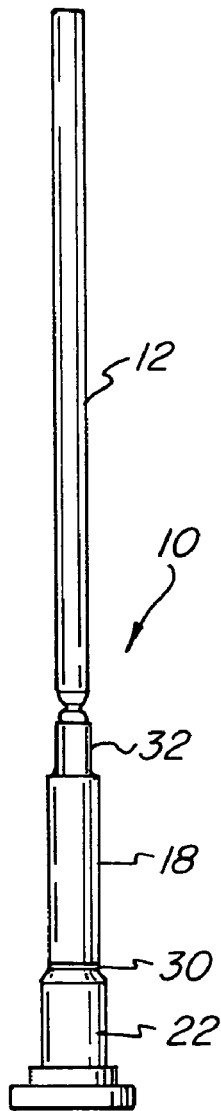
FIGS. 3A-C schematically illustrate the present invention and its method of use.

FIG. 1 is an elevational view illustrating the applicator and material dispensing system of the present invention. An applicator 12 has an elongated tubular handle, an applicator retaining portion 14, and an applicator end 16. The applicator end 16 may be made from any conventional applicator material such as cotton, foam, flock, or bristles. The applicator end 16 and the applicator retaining portion 14 are initially placed within an applicator holder 18 having an applicator chamber 20. The inside diameter of the applicator chamber 20 is sized slightly smaller than the exterior diameter of the applicator retaining portion 14 so as to provide a secure friction fit or interference fit within the applicator chamber 20. This permits the applicator 12 to be securely held within the applicator holder 18. One end of the applicator holder 18 is frangibly connected to a material holder 22 by frangible portion 30. The frangible portion 30 is a reduced thickness portion or scribe line. The material holder 22 has a material chamber 24 formed therein that contains a material 26. The material 26 may be any material, such as a liquid, gel, or powder that is desired to be applied by the applicator 12. Preferably, the material 26 is a medicament such as a dental material that may be used in a dental procedure, for example a liquid dental desensitizer, etch, or bonding agent. The bottom end of the material chamber is sealed with a flange 28. The flange 28 also has a relatively broad base so that the material holder 22 may be placed on a surface and held in an upright position. The other top end of the material chamber 24 is initially sealed adjacent the frangible portion 30 by a bottom end of the applicator holder 18. The top open end of the applicator holder 18 contains an external stopper or seal 32. The stopper or seal 32 has an outside diameter that is adapted or sized to fit within the open end of the material chamber 24 once the applicator holder 18 is frangibly severed there from.

The applicator and material dispensing system 10 may be made of any suitable plastic material by conventional techniques, such as injection molding. The flange 28 that seals the bottom portion of the material chamber 24 may be sonically welded or glued to the material holder 22 after the material chamber 24 is filled with a material 26. The applicator holder and the material holder preferably are cylindrical or have a circular lateral cross section, but may be of any shape.

FIG. 2 is a partial cross section illustrating applying a material to the applicator end 16 of the applicator 12. Upon removal of the applicator holder 18 by severing the frangible portion 30, illustrated in FIG. 1, an opening 34 is formed, unsealing the material chamber 24, in the material holder 22. Upon removal of the applicator 12 from the applicator holder 18 illustrated in FIG. 1, the applicator end 16 of the applicator 12 may enter the material chamber 24 through opening 34 so as to apply the material 26 onto the applicator end 16. The applicator end 16 may be then used to apply the material 26 to any desired surface.

Figure 3B:
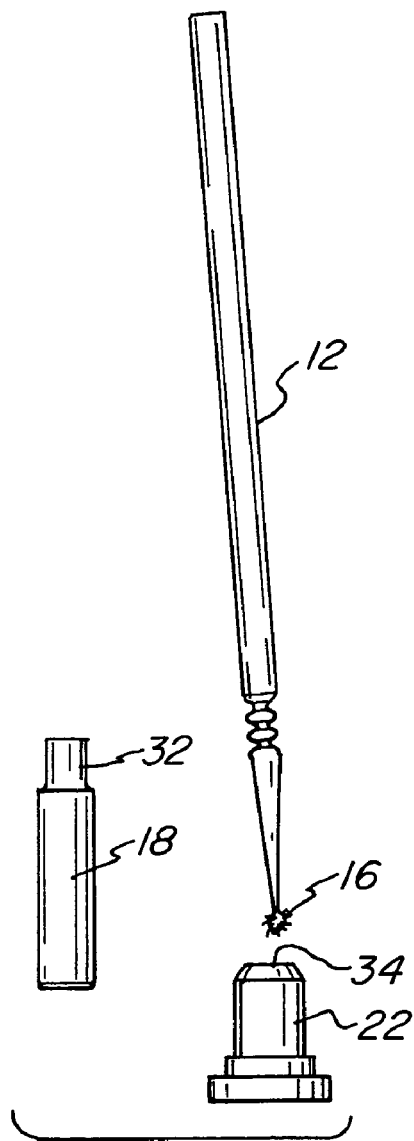
Figure 3C:
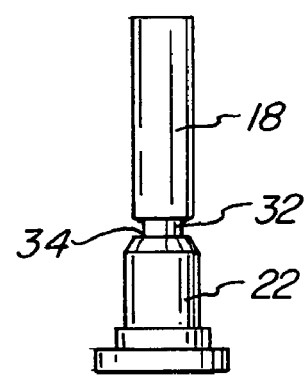

FIGS. 3A-C schematically illustrate the sequence or method of operation in using the applicator and material dispensing system 10 of the present invention. In FIG. 3A, the applicator 12 is illustrated being held within the applicator holder 18. The applicator holder 18 is initially frangibly connected to the material holder 22 by the frangible portion 30.

FIG. 3B illustrates the breaking or removing of the applicator holder 18 from the material holder 22 forming opening 34 in the material holder 22 through which the applicator end 16 of the applicator 12 may be placed. The opening 34 exposes the material contained within the material holder 22 permitting its placement on the applicator end 16.

FIG. 3C illustrates a feature of the present invention utilized to seal opening 34 in the opened material holder 22 by inserting the end of the applicator holder 18 having the reduced diameter or stopper 32 placed thereon into the opening 34 so as to seal the opening 34. The outside diameter of the stopper 32 is adapted so as to form a friction or interference fit with the opening 34. Therefore, the material contained within the material holder 22 may be effectively resealed by one end of the applicator holder 18.

FIG. 4 is a perspective view illustrating another embodiment of the present invention. In this embodiment, two different materials may be held so as to be mixed together prior to application with the applicator. The applicator and material dispensing system 110 comprises an applicator and first material holder 118. The applicator and first material holder 118 has an opening 136 therein. An applicator, not shown in FIG. 4, is placed through opening 136 and held by the applicator and first material holder 118 similarly to that illustrated in FIG. 1. Adjacent the opening 136 is a stopper or seal 132. A flange 129 is placed adjacent a frangible portion 130 and a second material holder 122. A sealing flange 128 may be used to seal one end of the material holder 122.

A first material, such as a powder, may be placed within the applicator and first material holder 118 prior to insertion of an applicator, not illustrated, into the opening 136. The applicator, not illustrated, would then seal the first material within the applicator and first material holder 118. A second material may be held in the second material holder 122. The second material may, for example, be a liquid. Upon separating, the applicator and first material holder 118 from the second material holder 122 at the frangible portion 130, the powder in the applicator and first material holder 118 may be placed within the second material holder 122. The seal or stopper 132 may be used to seal the now opened second material holder 122 to permit the two combined materials to be shaken together so as to thoroughly mix them. After mixing, the applicator and first material holder 118 may be removed from the second material holder 122 and an applicator, not illustrated, placed through the opening in the second material holder 122 to dispense the mixed first and second material contained therein. The second material holder 122 may have an opening larger than the inside diameter of the applicator and first material holder 118, so as to permit easy insertion of an applicator. Clearly, the sequence of mixing may be reversed so that the two materials are mixed and held in the applicator and first material holder 118 for dispensing.

FIG. 5 illustrates the use of the applicator and first material holder 118 as a stand for the applicator 112. After an initial application of material, the applicator 112 may be held upright, preventing contact of the application end 116 with a surface and possible contamination, by placing one end thereof into opening 136 of the applicator and first material holder 118. Additionally, the end of the applicator 112 may be used as a stopper to seal the material within the applicator and first material holder 118 between uses.

FIG. 6 illustrates another embodiment of the present invention. This embodiment has a slightly different construction than the other embodiments. The applicator and material dispensing system 210 comprises an applicator 212 placed within an applicator holder 218. The applicator holder 218 has an applicator retaining portion 214 and an applicator end 216. The applicator retaining portion 214 is held within the applicator chamber 220 by a friction or interference fit, or other retaining means. Formed on one end of the applicator holder 218 is a cap 219. The cap 219 is frangibly connected to the applicator holder 218 by a frangible portion 230. An opening passage 234 extends through the cap 219, the frangible portion 230, and into the applicator holder 218. The cap 219 is attached to a material holder 222. The material holder 222 has a material chamber 224 containing a material 226 therein. Attached to one end of the material holder 222 is a flange 228.

In this embodiment, the applicator material dispensing system 210 is made of three pieces; the applicator 212, the applicator holder 218, and the material holder 222. The cap 219, after insertion of the material 226 into the material holder 222, is sonically welded, glued, or otherwise attached, sealing the material within the material holder 222. When the material is desired to be used or applied, the applicator holder 218 is separated from the material holder 222 by breaking the frangible portion 230. Upon breaking the frangible portion 230, the opening passage 234 is exposed, permitting access to the material chamber 224 and the material 226 contained therein. The applicator 212 may then be removed from the applicator holder 218 and the applicator end 216 placed through the exposed opening passage 234 to access the material 226.

Figure 7:
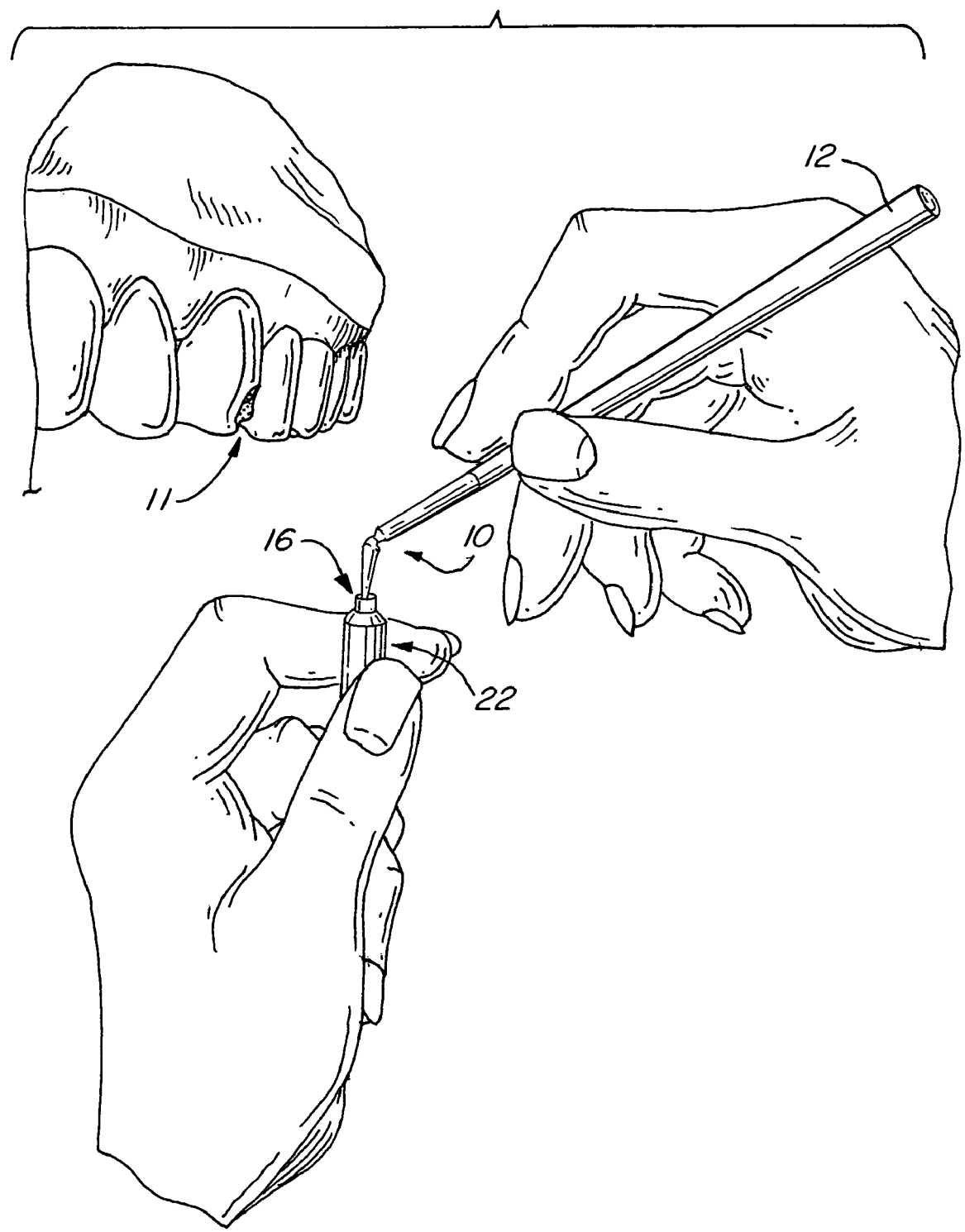
FIG. 7 schematically illustrates the application of the applicator and material dispensing system of the present invention to a dental procedure.

FIG. 7 illustrates the application of the present invention to a dental procedure. Upon separating the applicator holder, not illustrated, from the material holder 22, the applicator end 16 of the applicator 12 may be placed within the material holder 22 and used to apply a dental material to a tooth 11.

The present invention provides an applicator and material dispensing system that may be relatively inexpensively manufactured and is able to hold securely an applicating end of an applicator so as to prevent its contamination or contact with a material prior to use. The material to be applied is securely held within the initially attached material chamber, keeping it free from contamination and contact with the applicator end until just prior to application. Small quantities of material may be applied in a cost efficient unit dose manner so as to prevent cross contamination and waste of material, which may be relatively expensive. The present invention is well suited to applications of medicament or dental materials.

While the present invention has been described with respect to several preferred embodiments, it will be obvious to those skilled in the art that various modifications may be made without departing from the spirit and scope of this invention.

What is claimed is:

1. An applicator and material dispensing system comprising:
   an applicator;
   an applicator holder having an open end and a sealed end, the open end adapted to receive said applicator; and
   a material holder frangibly attached to the sealed end of said applicator holder so as to form an opening upon removal from the sealed end of said applicator holder exposing a material chamber and wherein said applicator is separated from the material chamber when said applicator is placed within said applicator holder and when said material holder is attached to said applicator holder;
   whereby upon separation of the applicator holder from said material holder, a material contained within the material holder is accessible through the opening, permitting the applicator to be used to apply the material.

2. An applicator and material dispensing system as in claim 1 wherein:
   said applicator comprises an applicator end having flock.

3. An applicator and material dispensing system as in claim 1 wherein:
   said applicator comprises an applicator end having bristles.

4. An applicator and material dispensing system as in claim 1 wherein:
   said applicator comprises an applicator end having foam.

5. An applicator and material dispensing system as in claim 1 further comprising:
   a material placed within the material holder.

6. An applicator and material dispensing system as in claim 5 wherein:
   said material comprises a dental material.

7. An applicator and material dispensing system as in claim 1 further comprising:
   a reduced diameter portion formed adjacent the open end of said applicator holder, whereby said reduced diameter portion is capable of acting as a stopper when placed in the opening in said material holder.

8. An applicator and material dispensing system as in claim 1 further comprising:
   a frangible portion placed between said applicator holder and said material holder.

9. An applicator and material dispensing system as in claim 8 wherein:
   said frangible portion comprises a reduced lateral dimension section.

10. An applicator and material dispensing system for dispensing a unit dose of material comprising:
    an applicator holder having an applicator chamber with an open end and a sealed end;
    a material holder attached to the sealed end of said applicator holder, said material holder having a material chamber;
    a material placed within the material chamber;
    a frangible portion placed between said applicator holder and said material holder so as to form an opening in said material holder providing access to the material chamber upon removal of said material holder from the sealed end of said applicator holder; and
    an applicator frictionally retained within the applicator chamber of said applicator holder, wherein said applicator and the applicator chamber are held separated from said material placed within the material chamber by said frangible portion,
    whereby upon separation of said applicator holder from said material holder, said material contained within said material chamber is accessible permitting said applicator to be used to apply said material.

11. An applicator and material dispensing system as in claim 10 wherein:
    a diameter of said material chamber is larger than a diameter of said applicator chamber.

12. An applicator and material dispensing system as in claim 10 wherein:
    said applicator comprises an applicator end having flock.

13. An applicator and material dispensing system as in claim 10 wherein:
    said applicator comprises an applicator end having bristles.

14. An applicator and material dispensing system as in claim 10 wherein:
    said applicator comprises an applicator end having foam.

15. An applicator and material dispensing system as in claim 10 wherein:
    said material comprises a dental material.

16. A unit dose applicator and material dispensing system comprising:
    an applicator holder having an applicator chamber with an open end and a sealed end, said applicator chamber having a first diameter;
    a material holder initially attached to the sealed end of said applicator holder, said material holder having an initially sealed material chamber with a second diameter, the second diameter being larger than the first diameter;
    a reduced diameter frangible portion placed between said applicator holder and said material holder so as to form an opening in said material holder providing access to said material chamber upon removal of said material holder from the sealed end of said applicator holder;

a material placed within said material holder; and an applicator frictionally retained within the applicator chamber of said applicator holder, wherein said applicator and said applicator holder are separated from said material placed within said material holder by said reduced diameter frangible portion preventing said applicator from contacting said material within said material holder until said material holder is removed from said applicator holder, whereby upon separation of said applicator holder from said material holder, said material placed within said material holder is accessible through the opening in said material holder, permitting the applicator to be used to apply said material.

17. An applicator and material dispensing system as in claim 16 wherein:

said applicator comprises an applicator end having flock.

18. An applicator and material dispensing system as in claim 16 wherein:

said applicator comprises an applicator end having bristles.

19. An applicator and material dispensing system as in claim 16 wherein:

said applicator comprises an applicator end having foam.

20. An applicator and material dispensing system as in claim 16 wherein:

said material comprises a dental material.

21. An applicator and material dispensing system as in claim 16 further comprising:

a flange placed on said material holder, whereby said material holder is capable of standing upright.

* * * * *